(12) United States Patent
Chien et al.

(10) Patent No.: US 7,622,506 B2
(45) Date of Patent: Nov. 24, 2009

(54) NAPHTHALENEDIONE COMPOUNDS FOR TREATING INFLAMMATION RELATED DISORDERS AND MICROBIAL INFECTION

(75) Inventors: Du-Shieng Chien, Guilford, CT (US); Yi-Wen Chu, Hsi-Chih (TW); Wu-Chang Chuang, Yonghe (TW); Ming-Chung Lee, Tucheng (TW)

(73) Assignee: SunTen Phytotech Co., Ltd., Jhonghe (TW)

( * ) Notice: Subject to any disclaimer, the term of this patent is extended or adjusted under 35 U.S.C. 154(b) by 0 days.

(21) Appl. No.: 11/733,028

(22) Filed: Apr. 9, 2007

(65) Prior Publication Data
US 2007/0238782 A1 Oct. 11, 2007

Related U.S. Application Data

(60) Provisional application No. 60/790,259, filed on Apr. 7, 2006.

(51) Int. Cl.
*A61K 31/21* (2006.01)
*A61K 31/122* (2006.01)

(52) U.S. Cl. ........................ 514/682; 514/510; 514/866; 514/887; 514/928

(58) Field of Classification Search ........................ None
See application file for complete search history.

(56) References Cited

U.S. PATENT DOCUMENTS

2005/0222258 A1* 10/2005 Wang

FOREIGN PATENT DOCUMENTS

| CN | 02114973.9 | 9/2004 |
| CN | 03128742.5 | 11/2004 |
| CN | 200310109057.7 | 8/2006 |

OTHER PUBLICATIONS

"Psoriasis", The Columbia Encyclopedia, 2004, Columbia University Press, downloaded from "http://.www.credoreference.com/entry/4294839", p. 1 of 1.*
Lee, "Helicobacter Pylori", MedicineNet.com, 2005, downloaded from "http://www.medicinenet.com/helicobacter_pylori/article.htm" on Dec. 24, 2008, pp. 1-4 of 4.*
Cihakova, Johns Hopkins Medical Institutions: Autoimmune Disease Research Center, "Type 1 Diabetes Mellitus", 2001, downloaded from "http://autoimmune.pathology.jhmi.edu/diseases.cfm?systemid=3&diseaseid=23", pp. 1-5 of 5.*
Caballero et al., Journal of Foot & Ankle Surgery, 1998, vol. 37(3), pp. 248-255.*
Assimopoulou et al. "Analysis of alkannin derivatives from *Alkanna* species by high-performance liquid chromatography/photodiode array/mass spectrometry", *Biomedical Chromatography*, Published online in Wiley InterScience (www.interscience.wiley.com) DOI:10.1002/bmc.705.
Chen et al. "Shikonin, a Component of Chinese Herbal Medicine, Inhibits Chemokine Receptor Function and Suppresses Human Immunodeficiency Virus Type 1", *Antimicrobial Agents and Chemotherapy*, Sep. 2003. pp. 2810-2816.
Davisson et al. "Phosphorylation of Isoprenoid Alchohols", *Journal of Organic Chemistry*, 1986, 51, pp. 4768-4779.
Kundakovic et al. "Cytotoxicity in vitro of Naphthazarin Derivatives from *Onosma arenaria*", *Phytotherapy Research*, 20, pp. 602-604 (2006).
Papageorgiou et al. "Recent Advances in Chemistry, Biology and Biotechnology of Alkannins and Shikonins", *Current Organic Chemistry*, 2006, 10, pp. 2123-2142.
Plyta et al. "Inhibition of Topoisomerase I by Naphthoquinone Derivatives", *Bioorganic & Medicinal Chemistry Letters*, 8 (1998) p. 3385-3390.
Shen et al. "Antimicrobial Activities of Naphthazarins from *Arnebia euchroma*", *J. Nat. Prod.*, 2002, 65, pp. 1857-1862.
Shukla et al. "Naphthaquinones of *Arnebia nobilis*" *Phytochemistry*, 1971, vol. 10, pp. 1909-1915.
Assimopoulou et al. "Analysis of alkannin derivatives from *Alkanna* species by high-performance liquid chromatography/photodiode array/mass spectrometry", *Biomedical Chromatography*, Published online in Wiley InterScience (www.interscience.wiley.com) DOI:10.1002/bmc.705, 2006.

* cited by examiner

*Primary Examiner*—Ardin Marschel
*Assistant Examiner*—Gregg Polansky
(74) *Attorney, Agent, or Firm*—Occhiuti Rohlicek & Tsao LLP

(57) ABSTRACT

This invention relates to compositions containing a compound of formula (I) shown below:

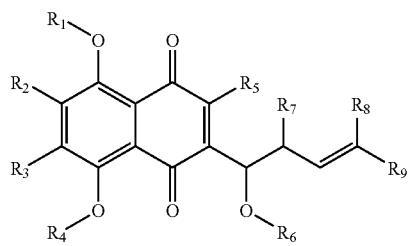

Each variable is defined in the specification. Also disclosed are methods of using these compositions to treat acne, psoriasis, and infective skin ulcer.

1 Claim, No Drawings

NAPHTHALENEDIONE COMPOUNDS FOR TREATING INFLAMMATION RELATED DISORDERS AND MICROBIAL INFECTION

RELATED APPLICATIONS

This application claims priority to U.S. Provisional Application No. 60/790,259, filed on Apr. 7, 2006, the contents of which are incorporated herein by reference.

BACKGROUND

Inflammation is the body's defense response to injury, infection, or antigenic stimulation. Under certain conditions, inflammation persists well after removal of the causal agents. For example, it often co-exists with dermatitis, asthma, and angiogenesis-related indications. A number of therapeutics have been developed for inhibiting unwanted inflammatory reactions. Nonetheless, many of them are not satisfactory due to poor efficacy or side effects. Thus, there remains a demand for a new treatment for unwanted inflammation.

Microbial infection is a major cause of inflammation. For example, infection with *Propionibacterium acnes* leads to acne vulgaris (pimples), skin ulcer, and associated inflammation. Antibiotics are commonly used for treating infection caused by *P. acnes* or other microbes. However, as the microbes tend to develop resistance, new therapeutic agents are still being sought for treating microbial infection.

SUMMARY

This invention relates to methods and compositions for treating inflammation related disorders or microbial infections.

In one aspect, this invention features a method of inhibiting the activity of 5-lipoxygenase, or treating acne, psoriasis, chronic atopic dermatitis, or infective skin ulcer with a naphthalenedione compound of formula (I):

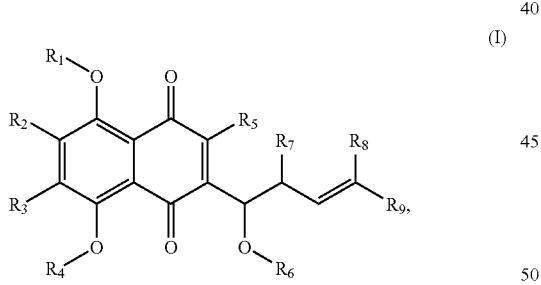

in which each of each of $R_1$ and $R_4$, independently, is H, $C_1$-$C_6$ alkyl, or $C(O)R_a$; each of $R_2$, $R_3$, $R_5$, and $R_7$, independently, is H, halogen, cyano, aminothio, C1-C6 alkylsulfonyl, C1-C6 arylsulfonyl, $C_1$-$C_6$ alkyl, $OR_b$, $SR_b$, or $NHR_b$; $R_6$ is $C_1$-$C_6$ alkyl or $C(O)R_c$; and each of $R_8$ and $R_9$, independently, is H, halogen, cyano, aminothio, C1-C6 alkylsulfonyl, C1-C6 arylsulfonyl, $C_1$-$C_6$ alkyl, or $OR_d$; in which each of $R_a$ and $R_c$, independently, is $C_1$-$C_6$ alkyl; and each of $R_b$ and $R_d$, independently, is H or $C_1$-$C_6$ alkyl.

Referring to formula (I), a subset of the naphthalenedione compounds described above are those in which $R_6$ is $C(O)R_c$. In these compounds, $R_c$ can be $CH_3$, $CH(CH_3)_2$, $CH=CH(CH_3)_2$, or $CH(CH_3)(CH_2CH_3)$; each of $R_1$, $R_2$, $R_3$, $R_4$, $R_5$ and $R_7$ can be H; and each of $R_8$ and $R_9$ can be $CH_3$. Exemplary naphthalenedione compounds include:

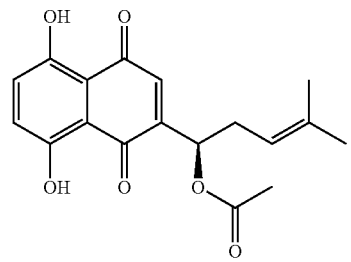

(R)-1-(5,8-dihydroxy-1,4-dioxo-1,4-dihydronaphthalen-2-yl)-4-methylpent-3-enyl acetate

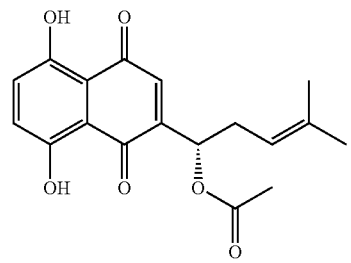

(S)-1-(5,8-dihydroxy-1,4-dioxo-1,4-dihydronaphthalen-2-yl)-4-methylpent-3-enyl acetate

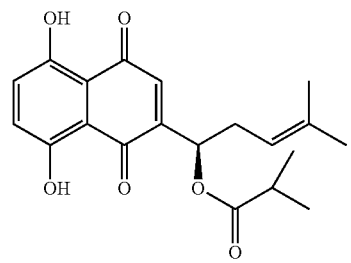

(R)-1-(5,8-dihydroxy-1,4-dioxo-1,4-dihydronaphthalen-2-yl)-4-methylpent-3-enyl isobutyrate

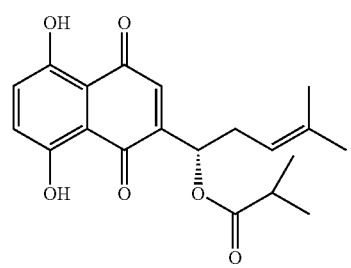

(S)-1-(5,8-dihydroxy-1,4-dioxo-1,4-dihydronaphthalen-2-yl)-4-methylpent-3-enyl isobutyrate

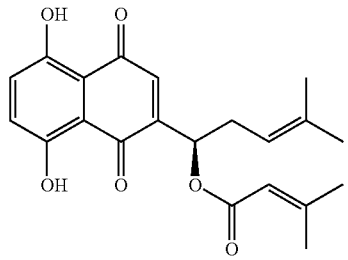

(R)-1-(5,8-dihydroxy-1,4-dioxo-1,4-dihydronaphthalen-2-yl)-4-methylpent-3-enyl 3-methylbut-2-enoate

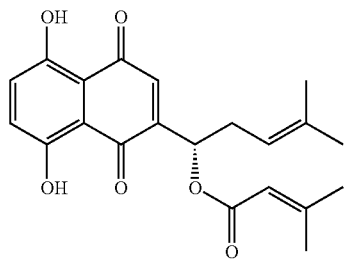

(S)-1-(5,8-dihydroxy-1,4-dioxo-1,4-dihydronaphthalen-2-yl)-4-methylpent-3-enyl 3-methylbut-2-enoate

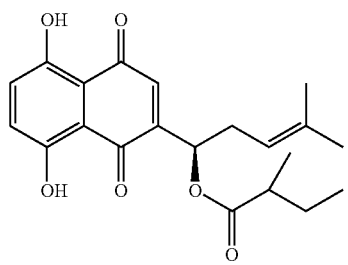

(R)-1-(5,8-dihydroxy-1,4-dioxo-1,4-dihydronaphthalen-2-yl)-4-methylpent-3-enyl 2-methylbutanoate, and

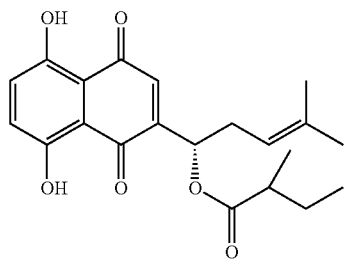

(S)-1-(5,8-dihydroxy-1,4-dioxo-1,4-dihydronaphthalen-2-yl)-4-methylpent-3-enyl 2-methylbutanoate The term "alkyl" refers to a saturated or unsaturated, linear or branched hydrocarbon moiety, such as —$CH_3$, —$CH_2$—CH=$CH_2$, or branched —$C_3H_7$. Alkyl groups mentioned herein include both substituted and unsubstituted moieties. Possible substituents on alkyl groups include, but are not limited to, $C_2$-$C_{10}$ alkenyl, $C_2$-$C_{10}$ alkynyl, $C_3$-$C_8$ cycloalkyl, $C_5$-$C_8$ cycloalkenyl, $C_3$-$C_{20}$ cycloalkyl, $C_1$-$C_{20}$ heterocycloalkyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester.

The aforementioned naphthalenedione compounds can also be used in treating infection with a microbe, e.g., *Propionibacterium acne*, or promoting recovery from skin ulceration caused by microbial infection. Examples of the infection also include pustular dermatitis. Specifically, one can administer to a subject in need thereof an effective amount of such a naphthalenedione compound or composition.

Also within the scope of this invention are (1) use of the compounds described above in treating a 5-lipoxygenase mediated skin disease (e.g., psoriasis and chronic atopic dermatitis) or microbe infection (e.g., acne), or treating infective skin ulcer; and (2) use of the compound in manufacture of a medicament for the just-mentioned applications.

The details of one or more embodiments of the invention are set forth in the description below. Other features, objects, and advantages of the invention will be apparent from the description and the claims.

DETAILED DESCRIPTION

This invention is based in part on the unexpected finding that certain naphthalenedione compounds are effective in inhibiting 5-lipoxygenase and in inhibiting the growth of a number of microbes. This enzyme is present in certain cells, e.g., those producing leukotrienes). It is a key enzyme essential to the bio-synthesis of leukotrienes, important mediators in inflammatory and allergic processes. Accordingly, these naphthalenedione compounds can be used to treat inflammatory disorders, e.g., inflammation-related dermatitis, by inhibiting 5-lipoxygenase activity.

Accordingly, within the scope of this invention is a composition that contains a suitable carrier and one or more of the naphthalenedione compounds described in the Summary section above. The composition can be a pharmaceutical composition that contains a pharmaceutically acceptable carrier or a cosmetic composition that contains a cosmetically acceptable suitable carrier. Preferably, a naphthalenedione compound is added to the composition in pure form. A pure compound refers to a compound substantially free of naturally associated molecules, i.e., at least 75% pure by dry weight. Purity can be measured by any appropriate standard method, for example, by HPLC analysis. The naphthalenedione compound described above can be chemically synthesized or purified from herbs. For example, it can be isolated from plants of the Boraginaceae family, including *Arnebia euchroma* (Royle) Johnst., *Lithospermum erythrorhizon* Sieb. et Zucc., *Lappula myosotis* V. Wolf, and *Onosma paniculatum* Bur. et Franch.

Examples of compositions of the present invention include, but are not limited to, foods, food additives, nutritional supplements, and cosmetic and pharmaceutical preparations. It may be in the form of tablets, suspensions, implants, solutions, emulsions, capsules, powders, syrups, liquid compositions, ointments, lotions, creams, pastes, gels, or the like.

As a dietary supplement, additional nutrients, such as minerals or amino acids, may be included. A dietary composition can also be a drink or food product. As used herein, the terms "drink" and "food" broadly refer to any kinds of liquid and solid/semi-solid materials, respectively, that are used for nourishing an animal, and for sustaining normal or accelerated growth of an animal including a human. Examples of the drink product include, but are not limited to, tea-based beverages, juice, coffee, and milk. Examples of the food product include jelly, cookies, cereals, chocolates, snack bars, herbal extracts, dairy products (e.g., ice cream, and yogurt), soy bean product (e.g., tofu), and rice products.

A composition of the present invention may include a carrier. Depending on the kind of the composition, a carrier may be a suitable dietary carrier, cosmetic carrier, or a pharmaceutically acceptable carrier. Examples of a pharmaceutically acceptable carrier include, but are not limited to, biocompatible vehicles, adjuvants, additives, and diluents to achieve a composition usable as a dosage form.

A "pharmaceutically acceptable carrier," after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active naphthalenedione compound. Examples of other carriers include colloidal silicon oxide, magnesium stearate, cellulose, sodium lauryl sulfate, and D&C Yellow #10.

The above-described composition, in any of the forms described above, can be used for treating inflammation-related disorders or infections with a number of microbes. For example, it can be used in treating macular eruptions, measles, sore-throat, carbuncles, burns, anal ulcers, diabetic foot ulcer, hemorrhoids, infected crusts, bedsores, external wounds, or oozing dermatitis. The term "treating" refers to the administration of an effective amount of a composition of the invention to a subject who has one of the above-described diseases or conditions, a symptom of such a disease, or a predisposition toward such a disease or condition, with the purpose to confer a therapeutic effect, e.g., to cure, relieve, alter, affect, ameliorate, or prevent the disease or condition, the symptom of it, or the predisposition toward it.

An inflammation-related disorder is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), psoriasis, asthma, and allergic rhinitis. Examples also include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, allograft rejection, and graft-versus-host disease), Sjogren's syndrome, human immunodeficiency virus infection, cancer (e.g., brain, breast, prostate, colon, kidney, ovary, thyroid, lung, and haematopoietic cancer), and tumor metastasis.

An "effective amount" refers to the amount of an active naphthalenedione compound that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrastemal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants or stabilizers such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having an active naphthalenedione compound can also be administered in the form of suppositories for rectal administration.

A topical composition contains a safe and effective amount of a dermatologically acceptable carrier suitable for application to the skin. Generally, a topical composition can be solid, semi-solid, cream, or liquid. It may be a cosmetic or dermatologic product in the form of an ointment, lotion, foam, cream, gel, emulsion, suspension or solution. Details about dermatologically acceptable carriers are provided below.

The naphthalenedione compounds described above can be preliminary screened for their efficacy in treating above-described diseases by an in vitro assay (See Examples 1-5 below) and then confirmed by animal experiments and clinical trials. Other methods will also be apparent to those of ordinary skill in the art.

A composition of the present invention may be used alone or in combination with other biologically active ingredients. Alone or in combination with other active ingredients, it may be administered to a subject in a single dose or multiple doses over a period of time. Various administration patterns will be apparent to those skilled in the art. The dosage ranges for the administration of the composition are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

Also within the scope of this invention is a cosmetic composition. This composition contains a safe and effective amount of a dermatologically acceptable carrier that is suitable for topical application to the skin. It enables an active naphthalenedione compound and optional component to be delivered to the skin at an appropriate concentration(s). The carrier can thus act as a diluent, dispersant, solvent, or the like to ensure that the active materials are applied to and distributed evenly over the selected target at an appropriate concentration. The carrier can be solid, semi-solid, or liquid. Preferably, it is in the form of a lotion, a cream, or a gel, in particular one that has a sufficient thickness or yield point to prevent the active materials from sedimenting. The carrier can be inert or possess dermatological benefits of its own. It should also be physically and chemically compatible with the active components described herein, and should not unduly impair stability, efficacy, or other use benefits associated with the composition.

The type of carrier utilized in the cosmetic composition depends on the type of product form of the composition. A cosmetic composition may be made into a wide variety of product forms such as those known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

Preferred carriers can contain a dermatologically acceptable hydrophilic diluent. Suitable hydrophilic diluents include water, organic hydrophilic diluents, such as $C_1$-$C_4$ monohydric alcohols and low molecular weight glycols and polyols (including propylene glycol, polyethylene glycol of, e.g., MW 200-600), polypropylene glycol of, e.g., MW 425-2025, glycerol, butylene glycol, 1,2,4-butanetriol, sorbitol esters, 1,2,6-hexanetriol, ethanol, iso-propanol, sorbitol esters, ethoxylated ethers, propoxylated ethers, and combinations thereof. The composition preferably comprises at least about 60% of the hydrophilic diluent.

Preferred carriers also contain an emulsion having a hydrophilic phase, especially an aqueous phase, and a hydrophobic phase, e.g., a lipid, oil, or oily material. As well known to one skilled in the art, the hydrophilic phase will be dispersed in the hydrophobic phase, or vice versa, to form respectively hydrophilic or hydrophobic dispersed and continuous phases, depending on the composition ingredients. The term "dispersed phase," a term well-known to one skilled in the art, refers to a phase that exists as small particles or droplets suspended in and surrounded by a continuous phase. The dispersed phase is also known as the internal or discontinuous phase. The emulsion may be or contain (e.g., in a triple or other multi-phase emulsion) an oil-in-water emulsion or a water-in-oil emulsion such as a water-in-silicone emulsion. Oil-in-water emulsions typically comprise from 1% to 50% (preferably 1% to 30%) of the dispersed hydrophobic phase and from 1% to 99% (preferably from 40% to 90%) of the continuous hydrophilic phase; water-in-oil emulsions typically comprise from 1% to 98% (preferably from 40% to 90%) of the dispersed hydrophilic phase and from 1% to 50% (preferably 1% to 30%) of the continuous hydrophobic phase. The emulsion may also comprise a gel network, such as that described in G. M. Eccleston, Application of Emulsion Stability Theories to Mobile and Semisolid O/W Emulsions, Cosmetics & Toiletries, Vol. 101, November 1996, pp. 73-92, incorporated herein by reference. Preferred compositions herein are oil-in-water emulsions.

Preferred examples of a cosmetic composition of this invention have an apparent viscosity of from about 5,000 to about 200,000 mPa·s (centipoise). For example, preferred lotions have an apparent viscosity of from about 10,000 to about 40,000 mPa·s; and preferred creams have an apparent viscosity of from about 30,000 to about 160,000 mPa·s. Apparent viscosity can be determined using a Brookfield DVII RV viscometer, spindle TD, at 5 rpm, or the equivalent thereof. The viscosity is determined on a composition after the composition has been allowed to stabilize following its preparation, generally at least 24 hours under conditions of 25° C.±1° C. and ambient pressure after preparation of the composition. Apparent viscosity is measured with the composition at a temperature of 25° C.±1° C., after 30 seconds spindle rotation.

The cosmetic composition of the present invention is usually formulated to have a pH of 9.5 or below and in general have a pH in the range from 4.5 to 9, more preferably from 5 to 8.5. Some examples, particularly those containing an additional active agent such as salicylic acid, require a lower pH in order for the additional active to be fully efficacious. These compositions are usually formulated to have a pH of from 2.5 to 5, more preferably from 2.7 to 4.

The cosmetic composition may contain a wide variety of optional components, provided that such optional components are physically and chemically compatible with the essential components described herein, and do not unduly impair stability, efficacy, or other use benefits associated with the compositions. Optional components may be dispersed, dissolved, or the like in the carrier of the present compositions.

Exemplary optional components include emollients, oil absorbents, antimicrobial agents, binders, buffering agents, denaturants, cosmetic astringents, external analgesics, film formers, humectants, opacifying agents, perfumes, pigments, skin soothing and healing agents, preservatives, propellants, skin penetration enhancers, solvents, suspending agents, emulsifiers, cleansing agents, thickening agents, solubilising agents, waxes, sunscreens, sunless tanning agents, antioxidants and/or radical scavengers, chelating agents, anti-acne agents, anti-inflammatory agents, desquamation agents/exfoliants, organic hydroxy acids, vitamins, and natural extracts. Examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker,. Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993) can also be used in the present invention.

The cosmetic composition of the present invention is generally prepared by conventional methods known in the art of making topical compositions. Such methods typically involve mixing of the ingredients in one or more steps to a relatively uniform state, with or without heating, cooling, application of vacuum, and the like.

The cosmetic composition is useful for regulating or improving skin condition, including regulating visible or tactile wrinkles or discontinuities in skin, e.g., visible or tactile wrinkles or discontinuities in skin texture or color, more especially those associated with skin inflammation, ageing, or other internal factors (e.g., biochemical changes from within the skin) or external factors (e.g., ultraviolet radiation, environmental pollution, wind, heat, low humidity, harsh surfactants, and abrasives).

Regulating skin conditions can be carried out prophylactically or therapeutically. Prophylactical regulation includes delaying, minimizing, or preventing visible or tactile wrinkles or discontinuities in skin. Therapeutic regulation, on the other hand, includes ameliorating, diminishing, minimizing or effacing such wrinkles or discontinuities. Regulating skin conditions involves improving skin appearance feel, e.g., providing a smoother, more even appearance or feel and reducing signs of aging.

A cosmetic composition is topically applied to the skin in a safe and effective amount. The applied amount, the frequency of application, and the period of use vary widely depending upon the active levels of a given composition and the level of regulation desired. Typically, the composition can be applied once per day. However application rates can vary from about once per week up to about three times per day or more.

The cosmetic composition of this invention provides visible improvement in skin condition essentially immediately following application of the composition to the skin. Such immediate improvement involves covering or masking skin imperfections such as textural discontinuities (including those associated with skin inflammation or aging, e.g., enlarged pores), or providing a more even skin tone or color. The composition also provides visible improvement in skin condition following chronic topical application, e.g., one week, one year, or the subject's life time.

Regulating skin conditions is preferably performed by applying a composition in the form of a skin lotion, cream, cosmetic, or the like which is intended to be left on the skin for an extended period for some aesthetic, prophylactic, therapeutic or other benefits, i.e., a "leave-on" composition. After applying the composition to the skin, the "leave-on" composition is preferably left on the skin for a period of at least 15 minutes and up to 12 hours.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

A number of compounds were isolated from *Arnebia euchorma* (Royle) Johnst. Specifically, 1.65 kg of the herb was soaked in 32 L of acetone for 3 days before filtration through a 200 mesh filter. The filtrate was concentrated under vacuum to give a herbal extract. One hundred milligrams of this extract was dissolved in 50 ml 100% methanol. The solution was sonicated for 30 minutes and filtered through a 0.45 μm membrane. It was subjected to HPLC and eluted with 75% methanol. Six compounds were detected and separated by HPLC. Chromatographic conditions for the analytical HPLC were: mobile phase: (A) $H_2O$: $CH_3CN$: AcOH=800 ml: 200 ml: 10 ml, (B) $H_2O$: $CH_3CN$: MeOH: AcOH=100 ml: 450 ml: 450 ml: 1 ml; flow rate, 0.8 ml/min; detection wavelength, 515 nm; column temperature, 40° C.; gradient, linear from 10% B to 100% B; run time, 60 minutes.

For each compound, the fractions containing it were pooled. The solvent in the pooled fractions was removed under vacuum to give a residue. Each residue was partitioned between ethyl acetate and water. The aqueous fraction was discarded. Ethyl acetate was then removed under vacuum to give (R)-5,8-dihydroxy-2-(1-hydroxy-4-methylpent-3-enyl) naphthalene-1,4-dione ("SK"), (R)-1-(5,8-dihydroxy-1,4-dioxo-1,4-dihydronaphthalen-2-yl)-4-methylpent-3-enyl acetate ("ASK"), 5,8-dihydroxy-2-(4-methylpent-3-enyl) naphthalene-1,4-dione ("DSK"), (R)-1-(5,8-dihydroxy-1,4-dioxo-1,4-dihydronaphthalen-2-yl)-4-methylpent-3-enyl isobutyrate ("ISK"), (R)-1-(5,8-dihydroxy-1,4-dioxo-1,4-dihydronaphthalen-2-yl)-4-(methylpent-3-enyl β,β-dimethylacrylate ("BSK"), and 1-(5,8-dihydroxy-1,4-dioxo-1,4-dihydronaphthalen-2-yl)-4-methylpent-3-enyl 2-methylbutanoate ("MBSK"). Each of the isolated compounds was examined under a microscope for its color, shape, crystal form, and appearance. The results are summarized in Table 1 below:

TABLE 1

Compounds Isolated from *Arnebia euchorma*

| | SK | ASK | BSK | DSK | ISK | MBSK |
|---|---|---|---|---|---|---|
| Appearance | Crystalline needle | Crystalline needle | Oil | Crystalline powder | Crystalline powder | Oil |
| Color | Brown | Burgundy | Burgundy | Dark Red | Brown | Maroon |
| Retention Time on analytic HPLC (min) | 35.0 | 40.0 | 48.5 | 45.0 | 46.5 | 49.0 |

EXAMPLE 2

Effects of the above-mentioned compounds (1 or 10 μM) as well as extracts prepared from *Arnebia euchorma* on the activity of 5-Lipoxygenase were studied by a method modified from those described in Carter et al. J. Pharmacol. Exp. Ther., 1991, 256(3): 929-937, and Safayhi et al., Planta Medica, 2000, 66: 110-113). It was found that they inhibited the activity of 5-lipoxygenase. Nordihydroguaiaretic acid (NDGA), epigallocatechin-3 gallate (EGCG), and Ciclpirox Olamine were used as positive controls. The results are summarized in Tables 2A and 2B below:

TABLE 2A

Inhibition of 5-Lipoxygenase I

| Compounds | Concentration (μM) | % Inhibition | 5-Lipoxygenase, $IC_{50}$ (μM) |
|---|---|---|---|
| SK | 1 | 70 | 0.390 |
| SK | 10 | 101 | 0.390 |
| ASK | 10 | 99 | 1.46 |
| DSK | 10 | 53 | 7.01 |
| ISK | 10 | 98 | 1.54 |
| BSK | 10 | 99 | 1.2 |
| MSK | 10 | 98 | 1.37 |
| NDGA (reference) |  |  | 0.177 |

TABLE 2B

Inhibition of 5-Lipoxygenase II

| Compounds or Extracts | Concentration | % Inhibition | 5-Lipoxygenase, $IC_{50}$ |
|---|---|---|---|
| *Arnebia* extract | 1 μg/ml | 70 | 0.519 μg/ml |
| *Lithospermum* extract | 1 μg/ml | 64 | 0.625 μg/ml |
| EGCG | 100 μM | 58 | 87.2 μM |
| SK | 1 μg/ml | 51 | 0.845 μg/ml |
| DSK | 10 μg/ml | 64 | 5.47 μg/ml |
| Ciclpirox Olamine | 30 μM | 66 | 16.9 μM |
| NDGA (reference) |  |  | 0.113 μM |

5-Lipoxygenase has been known to be a key enzyme in the bio-synthesis of leukotrienes, important mediators in inflammatory and allergic processes. The results suggest that these compounds have dual anti-inflammatory and anti-allergic activities. The experiment was repeated using various concentrations of the compounds. Similar results were obtained.

EXAMPLE 3

The above-mentioned compounds and extracts were studied for their activities against *Propionibacterium acnes*, a causative bacterial agent of acne vulgaris (pimples). Specifically, inhibition by the compounds or extracts on the growth of the bacterium (ATCC6919) was examined by a method modified from those described in Modugno et al., Antimicrobial Agents and Chemotherapy, 1994, 38: 2362-2368 and Misiek et al., Antimicrobial Agents Chemtherapy, 1973, 3: 40-48 (1973). The results are summarized in Table 3 below.

TABLE 3

Anti-*Propionibacterium acnes* Activity

| Compounds | Dose (μg/ml) | Results |
|---|---|---|
| SK | 30 | + |
| SK | 10 | + |
| ASK | 10 | + |
| DSK | 10 | + |
| DSK | 3 | + |
| ISK | 30 | + |
| BSK | 30 | + |
| MBSK | 30 | + |
| *Arnebia* extract | 10 | + |
| Ciclpirox Olamine | 30 | + |

The results demonstrate that the above-mentioned compounds and extracts can be used in treating *Propionibacterium acnes* infections.

EXAMPLE 4

The above-mentioned compounds and extracts were studied for their activities against *Staphylococcus aureus*. *Staphylococcus aureus*, a bacterium that is a common coloniser of human skin and mucosa, can cause various skin infections, urinary tract infections, pneumonia, bacteraemia, and food poisoning. Although most strains of this bacterium are sensitive to many antibiotics (e.g., methicillin), some are resistant to the antibiotic.

In this example, the inhibition by the aforementioned compounds or extracts on the growth of methicillin-resistant *Staphylococcus aureus* (ATCC33591) was studied by a method modified from those described in Modugno et al., Antimicrobial Agents and Chemotherapy, 1994, 38: 2362-2368, and Misiek et al., Antimicrobial Agents Chemotherapy, 1973, 3: 40-48. The results are summarized in Table 4 below:

TABLE 4

Anti-methicillin-resistant *Staphylococcus aureus* Activity

| Compounds or Extracts | Dose (μg/ml) | Results |
|---|---|---|
| SK | 10 | + |
| SK | 3 | + |
| ASK | 1 | + |
| DSK | 10 | + |
| DSK | 3 | + |
| ISK | 3 | + |
| BSK | 1 | + |
| MBSK | 1 | + |
| *Arnebia* extract | 0.3 | + |
| *Lithospermum* extract | 1 | + |
| EGCG | 10 | + |
| Ciclpirox Olamine | 10 | + |

The results demonstrate that the above-mentioned compounds and extracts can be used in treating infections with *Staphylococcus aureus*, e.g., methicillin-resistant *Staphylococcus aureus* ("MRSA").

The above experiments on Staphylococcus aureus and *Propionibacterium acnes* were repeated using various concentrations of the compounds. Effective concentration ranges are summarized in Table 5 below:

TABLE 5

Anti-microbial Activity

| Compounds | Anti-microbial Activity | |
|---|---|---|
| | MRSA (μM) | P. acnes (μM) |
| SK | 10.4~34.7 | 34.7~104.1 |
| ASK | 0.9~3.0 | 3.0~30.3 |
| DSK | 7.8~26.0 | 7.8~26.0 |
| ISK | 7.7 | 77.4 |
| BSK | 2.8 | 83.7 |
| MBSK | 2.7 | 81.0 |
| Ciclopirox Olamine | 37.3 | 37.3~111.8 |
| Gentamicin | 2.1 | na |
| Ampicillin | na | 0.3 |

EXAMPLE 5

SK and ASK were studied for their activities against *Candida albicans*. *Candida albicans* (sometimes referred to as monilia) is a fungus that is normally present on the skin and in mucous membranes such as the vagina, mouth, or rectum. It also can travel through the blood stream and affect the throat, intestines, and heart valves. An infection with it causes thrush, diaper rash, vaginalitis moniliasis (commonly known as a yeast infection), candidal onchomycosis, paronychia, balanitis, and damages to the esophagus and the digestive tract. An infection in the bloodstream can affect the kidneys, heart, lungs, eyes, or other organs causing high fever, chills, anemia, and sometimes a rash or shock. Here, the inhibition by the aforementioned compounds or extracts on the growth of *Candida albicans* (ATCC 10231) was studied by a method modified from those described in Modugno et al. and Misiek et al., (supra). The results are summarized in Table 6 below:

TABLE 6

Anti-*Candida albicans* Activity

| Compounds | Dose (μg/ml) | Results |
|---|---|---|
| SK | 10 | + |
| ASK | 30 | + |

The results demonstrate that SK and ASK and extracts can be used in treating infections with *Candida albicans*.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating diabetic foot ulcer, comprising topically administering to a subject in need thereof with an effective amount of a compound selected from the group consisting of (R)-1-(5,8-dihydroxy-1,4-dioxo-1,4-dihydronaphthalen-2-yl)-4-methylpent-3-enyl acetate ("ASK") and 5,8-dihydroxy-2-(1-hydroxy-4-methylpent-3-enyl) naphthalene-1,4-dione ("SK").

* * * * *